US007640271B2

(12) United States Patent
Logan, Jr.

(10) Patent No.: US 7,640,271 B2
(45) Date of Patent: Dec. 29, 2009

(54) SYSTEM FOR MAINTAINING PATIENT MEDICAL RECORDS FOR PARTICIPATING PATIENTS

(76) Inventor: Carmen Logan, Jr., 60 E. Genesee St., Skaneateles, NY (US) 13152

( * ) Notice: Subject to any disclaimer, the term of this patent is extended or adjusted under 35 U.S.C. 154(b) by 320 days.

(21) Appl. No.: 11/413,727

(22) Filed: Apr. 28, 2006

(65) Prior Publication Data

US 2006/0206361 A1 Sep. 14, 2006

Related U.S. Application Data

(62) Division of application No. 10/828,144, filed on Apr. 21, 2004, now Pat. No. 7,039,628.

(51) Int. Cl.
*G06F 17/30* (2006.01)
*G06F 7/00* (2006.01)
(52) U.S. Cl. .................... 707/104.1; 707/10
(58) Field of Classification Search ............. 707/104.1, 707/10
See application file for complete search history.

(56) References Cited

U.S. PATENT DOCUMENTS 5,772,585 A * 6/1998 Lavin et al. ................. 600/300
6,476,833 B1 * 11/2002 Moshfeghi ................. 715/854
2001/0039504 A1 * 11/2001 Linberg et al. ................ 705/3
2003/0130873 A1 * 7/2003 Nevin et al. ................... 705/3
2003/0200119 A1 * 10/2003 Lewis et al. ................... 705/2
2003/0208382 A1 * 11/2003 Westfall ....................... 705/3
2004/0024616 A1 * 2/2004 Spector et al. ................ 705/2
2005/0080650 A1 * 4/2005 Noel .............................. 705/2

* cited by examiner

*Primary Examiner*—Kuen S Lu
(74) *Attorney, Agent, or Firm*—Bernhard P. Molldrem, Jr.

(57) ABSTRACT

A portable heath care records system employs a server on which the health care records of participating patients are stored. The patients may access the system using cards or CD-ROMS that are inserted into the patient's computer. The patients can review their own records via Internet and can edit them. The patient may also access via cell phone or handheld device. The patient record is protected by patient ID and password. Treating physicians have access to each patient's records for review and update. A two-way firewall permits patients to review their own health records only, but permits the physician to review both the physician files and the patient files. The physician can override the firewall to send patient information from his or her record. A read-only emergency screen with medical data about the patient may be accessed for emergency use. Records of many patients and of many clinics are maintained on a common server, so that the patient record can be accessed globally.

19 Claims, 21 Drawing Sheets

MDRS CARD
*Medical Data Recovery Source*

ACCOUNT INFORMATION FOR
CURRENT PATIENTS: [Carmen Login Jr ▾] (GO!)

A listing of current patients on this account appear in the list below. Click on the down arrow next to the first name in the list to view all the patients. Please select or highlight a member name from the list to view information then click on the GO! button.

If you would like to add a new patient to your account, please click on the Add New Patient button. A blank General Information form will display allowing you to begin entering the new patient's information.

After you have entered the required general information for the new patient, you may continue adding health information as desired.

(Add Patient)—62

FIG.5

| | |
|---|---|
| Home Main Patient Page Emergency Room View Reminders LogOut Help | |

GENERAL INFORMATION

The General Information form only needs to be completed once. However, it is highly recommended that you complete as much of the information as possible. Such information as telephone numbers, home address, social security number, employer information is vital information to recorded and up-to-date for family members.

Please update the information contained in this form as it changes.
Click on the Edit... button to open the form and modify the information.

PATIENT: CARMEN LOGAN JR.    Edit... ~60

- General Information
- Medical Information
- Physicians
- Insurance
- Visits
- Medications
- Allergies
- Diet
- Daily Living Aids
- Disabilities
- Family History
- Illnesses
- Immunizations
- Surgeries
- Diagnosis
- Advanced Directives
- Medical Notes
- Emergency Contacts Home Address    Day Phone    315-555-1111    Evening Phone    Cell Phone
60 E. Genesee St.                              315-555-1122    315-444-5555
Skaneateles, NY 13157

Employer         Title
MDRS             President/CEO

1110 W. Genesee St.    Phone    315-222-9595
Syracuse, NY 13290     Fax      315-222-9596

Email:           phjr1@aol.com
Date of Birth:   4/15/1937

FIG.6

GENERAL MEDICAL INFORMATION

Please complete the following questions then click on the Update button to save information. This general medical history will be especially helpful in the event of an emergency.

- General Information
- *Medical Information*
- ● Physicians
- Insurance
- Visits
- Medications
- Allergies
- Diet
- Daily Living Aids
- Disabilities
- Family History
- Illnesses
- Immunizations
- Surgeries
- Diagnosis
- Advanced Directives
- Medical Notes
- Emergency Contacts

PATIENT: CARMEN LOGAN JR.

Blood Type:    O Positive
Weight:    223
Height:    5ft. 10in.
Eye Color:    brown
Language:    english
Race:    italian/lebonese Edit...

FIG.7

| Home | Main Patient Page | Emergency Room View | Reminders | LogOut | Help |

- ○ General Information
- ● *Medical Information*
- ○ Physicians
- ○ Insurance
- ○ Visits
- ○ Medications
- ○ Allergies
- ○ Diet
- ○ Daily Living Aids
- ○ Disabilities
- ○ Family History
- ○ Illnesses
- ○ Immunizations
- ○ Surgeries
- ○ Diagnosis
- ○ Advanced Directives
- ○ Medical Notes:
- ○ Emergency Contacts Blood Type: [O Positive ▽]
Weight: [223] ⦿Pounds ○Kilograms
Height: [5ft. 10in.]
Eye Color: [brown]
Religion: [catholic]
Primary Language: [english]
Race: [italian/lebonese]
DO YOU USE/HAVE ANY OF THE FOLLOWING?
Contacts ○Yes ⦿No
Eye Glasses ○Yes ⦿No
Braces ○Yes ⦿No
Hearing Aid ○Yes ⦿No
Pacemaker ○Yes ⦿No
Prosthesis ○Yes ⦿No
Dentures ○Yes ⦿No
Do you smoke cigarettes? ○Yes ⦿No
Please describe usage: [            ]
Do you drink alcohol? ⦿Yes ○No
Please describe usage: [socially]
Are you recovering from an addiction? ○Yes ⦿No

FIG.8

| | | | | | | | |
|---|---|---|---|---|---|---|---|
| Home | Main Patient Page | Emergency Room View | Reminders | LogOut | Help | | |

EMERGENCY INFORMATION

○ General Information
○ Medical Information
● *Physicians*
○ Insurance
○ Visits
○ Medications
○ Allergies
○ Diet
○ Daily Living Aids
○ Disabilities
○ Family History
○ Illnesses
○ Immunizations
○ Surgeries
○ Diagnosis
○ Advanced Directives
○ Medical Notes
○ Emergency Contacts Date of Birth    Blood Type
4/18/1937        O Positive Emergency Contacts
Name:               Day Phone        Evening Phone    Cell Phone       Relationship
Clar Roth           315-555-1111     315-555-1122     315-457-444-5555 Health Care Proxy Primary Physician   Telephone
Dr. Rutko           555-7777

Allergy Name        Severity         Trigger
Aspirin-Medication  Mild

Medication Name     Dosage           Usage
Atrovent            2 Units PRN      Bronchodilation
Flonase             2puffs/morn      Control Nasal Area
Flovent             2puffs/morn      To open airways
Lipitor             20 mg/qd         Lower Cholesterol
Prilosec            10 mg/qd         Reflux
Singular            10 mg/qd         Control Nasal Area Medical Warning Notes
2/22/2001           do not administer aspirin ---
                    allergic administer Advil

FIG.9

| Home | Main Patient Page | Emergency Room View | Reminders | LogOut | Help |

IMMUNIZATIONS

To add a new immunization, click on the Add New...button. A blank form will display allowing you to enter new information for the immunization. Please complete as much of the information as possible to ensure for a complete medical history.

To edit an existing immunization, click on the Edit... button next to the desired immunization record. If you wish to delete an immunization history record, click on the Delete...button.

PATIENT: CARMEN LOGAN JR.

| Name | Age | Date | | |
|---|---|---|---|---|
| | | | | (Add New...) |
| H, influenzae Type b (Hib) | 63 | 11/16/2000 | (Edit...) | (Delete...) |
| Diphtheria, Tetanus, Pertussis (Dtap) | 63 | 12/4/2000 | (Edit...) | (Delete...) |
| Typhoid | 30 | 2/25/2001 | | |

- ○ General Information
- ○ Medical Information
- ○ Physicians
- ○ Insurance
- ○ Visits
- ○ Medications
- ○ Allergies
- ○ Diet
- ○ Daily Living Aids
- ○ Disabilities
- ○ Family History
- ○ Illnesses
- ● *Immunizations*
- ○ Surgeries
- ○ Diagnosis
- ○ Advanced Directives
- ○ Medical Notes
- ○ Emergency Contacts

*FIG.13*

| Home | Main Patient Page | Emergency Room View | Reminders | LogOut | Help |

ADVANCED DIRECTIVES

- General Information
- Medical Information
- Physicians
- Insurance
- Visits
- Medications
- Allergies
- Diet
- Daily Living Aids
- Disabilities
- Family History
- Illnesses
- Immunizations
- Surgeries
- Diagnosis
- Advanced Directives
- Medical Notes
- Emergency Contacts Advanced Directives include a Do Not Resuscitate (DNR) and Organ Donation. The information recorded here is for informational purposes only. Please consult your primary care physician for the proper forms to complete and where the forms should reside in case of emergency.

To enter information regarding a DNR Order and Organ Donation, click on Add Advanced Directive. Although we have combined the DNR Order and Organ Donation on the same form, you can only fill out one section of the form. If an Advanced Directive form exists, click on Edit to change or update the information.

To delete the Advanced Directive, click Delete. This action will permanently remove information for your Do Not Resuscitate Order and Organ Donation.

PATIENT: CARMEN LOGAN JR.

Advanced Directive exists ( Edit... )   ( Delete... )

FIG.14

| Home | Main Patient Page | Emergency Room View | Reminders | LogOut | Help |

○ General Information
○ Medical Information
○ Physicians
○ Insurance
○ Visits
○ Medications
○ Allergies
○ Diet
○ Daily Living Aids
○ Disabilities
○ Family History
○ Illnesses
○ Immunizations
○ Surgeries
○ Diagnosis
● *Advanced Directives*
○ Medical Notes
○ Emergency Contacts

DO NOT RESUSCITATE (DNR) ORDER

Indication of Do Not Resuscitate Order: ⦿ Yes ○ No

Location of DNR: [St. Joseph's Hospital]

ORGAN DONATION

Tissue:
☐ Cornea
☐ Heart Valves
☐ Bone Marrow
☐ Connective Tissue
☐ Skin

Organs:
☐ Heart
☐ Kidney(s)
☐ Liver
☐ Pancreas
☐ Lung(s)

Limitations or special wishes, if any (Update) (Delete...)

SYSTEM FOR MAINTAINING PATIENT MEDICAL RECORDS FOR PARTICIPATING PATIENTS

RELATED APPLICATION DATA

This is a Division of my application Ser. No. 10/828,144, filed Apr. 21, 2004, now U.S. Pat. No. 7,039,628, May 2, 2006.

BACKGROUND OF THE INVENTION

This invention is directed to a system for maintaining large number of patient medical records, for providing the patients with access to their personal records, and which can provide patient health and treatment records, including many categories of medical history, to the person's medical practitioner, using a network such as a local network, a wide area network, or a global computer network such as the Internet.

There is at present a need for real-time access to patient information. The availability of patient information to the practitioner can benefit the cost and quality of medical care, by speeding the examination process, eliminating duplicate testing, eliminating duplication of services, documenting physician care, and reducing the chance of mistake. At present, there is a lack of efficient patient information flow between segments of the healthcare industry. The patient information systems that are currently in use are either primarily physician-based, hospital-based, or insurance-based, and not patient-based. These systems are interactively limited, are quite expensive, and do not provide any simple access tool for the patient or for the medical community.

At present, it has been reported that physicians spend up to 58% of their time documenting patient care. Other research indicates that 30% of patient encounters now occur without the physician having access to the patient's charts. Also, as much as 90% of emergency department visits occur without the physician having any knowledge of the patient's medical history or prior medical treatments. At the same time, studies show that 11% of all medical laboratory testing is redundant and unnecessary, adding at least one billion dollars ($1,000,000,000) annually to America's medical costs. Other research indicates that about 33% of elderly admissions were the direct result of contraindicated drugs.

A number of computerized systems for tracking patient medical records have been previously proposed, but these do not address the problem of how to provide patients with access to a centralized repository of their medical records and health data. These prior systems do not provide the physicians that the patient may visit with the patient's medical history, allergies, medication data, or other important health data.

A prior approach, as discussed in McNerney Published Appln. US 2003/0088441, deals with a patient medical record system in which relevant patient medical information is accessed via a CD/ROM, with the records being stored at a central server. X-rays and prescriptions can be included in the medical records that are uploaded to the server. While the patient can access his or her own medical files, this requires using a special kiosk that is located at the healthcare provider's location, and the patient interface is basically limited to entering patient personal information.

Wilkins U.S. Pat. No. 6,523,099 relates to an individualized patient medical record system, where the patient can later review his or her own medical records. The patient carries a digital record on his or her person, with the entire medical record being stored on a portable data memory device, e.g., a CD-ROM.

What appears to be lacking in the previously proposed systems is a patient health care record system that is easily accessed, e.g., from a web site or by inserting a CD/ROM in to a computer, whereby the computer can automatically access the host server via the Internet, and where the patient can access his or her own files by inserting a PIN or other identifying password to access the patient's own complete medical history. The prior art also fails to show a system where the patient or emergency room personnel can obtain a limited, read-only version of the patient history without having the patient's PIN number. The prior proposed systems did not employ a two-way firewall that would permit the patient to read and modify his or her own records, but not the physician's records nor those of other patients, yet permits the physician to modify his own records plus the patient's records.

A number of adverse patient care problems arise from medical record unavailability or mismanagement. One recent study indicates that physicians devote a significant share of their time just to patient care documentation. By making it possible for the physician to devote a higher fraction of time to patient care, the level of care would improve without a cost increase. Also, an estimated 90% of emergency department visits occur without any knowledge of the patient records or of the patient's prior conditions. This can lead to many errors from misdiagnosis. Studies have also shown that 11% of laboratory testing is redundant, and not needed, which adds an additional one billion dollars to medical costs annually. Prescribing or administering contra-indicated drugs to the patient is also a problem, and recent research indicates that a third of all elderly admissions have been the direct result of contra-indicated drugs.

It would be desirable to allow access to the patient's medical records on any standard, general small computer, i.e. laptop or desk top personal computers, where the patient medical history is called up using the computer's Internet browser. The objective is to achieve a better patient throughput for the physician, as the physician would have the patient's entire medical history, including prior diagnoses, prescriptions, immunizations, allergies, and surgeries and procedures when meeting with the patient. The patient would have the ability to maintain the patient's own records, but the system would also allow the physician complete and accurate medical information, with the ability to update the patient's medical data. Having all prior procedures and diagnoses listed would improve accuracy of the medical data and medical histories of patients, and would eliminate unnecessary retesting. The treating physicians and pharmacists would have access to prior medication prescriptions and dosages for the patient, as well as patient allergy and reaction information. Knowledge of what other drugs the patient takes goes a long way towards eliminating the risk of life-threatening prescription interactions.

Desirably, the medical records should be accessible by the doctors or hospital personnel without requiring special training, with the physician's or other care provider's computer providing access to the patient's medical records.

At the present time, Medication Reconciliation is becoming to be recognized for its importance in keeping tabs on what pharmaceuticals patients are taking, both at home and in hospital. This is intended to help achieve the national patient safety goal, established by the Joint Commission on Accreditation of Healthcare Organizations, to have all hospitals establish procedures for accurately and completely reconciling medications across the continuum of health care. Medical reconciliation means that upon admission of patients, any medications taken prior to coming to the hospital would be identified by nursing staff and recorded. At present, a Medication Reconciliation Order Sheet (which is a paper form) is used for this purpose. The intention is to include prescription and sample medications, vitamins, vaccines, over-the-counter drugs, and even non-prescribed herbal preparations. The admitting physician or healthcare provider is then responsible for reviewing the patient's medication history, and reconciling the information on the medication history with any new medications that the physician might prescribe. This involves checking for medication interactions and making notes of any new prescriptions or changes to old ones.

This step is a recognition that each time that there is a transition in patient care, there is a potential for errors in medications. Medication Reconciliation upon transfer of a patient is supposed to prevent those errors by ensuring that subsequent healthcare providers are aware of the patient's condition and medication history. This requires constant attention to each patient's Medication Reconciliation file, as the file has to be updated each time the patient starts a new treatment or medication, or changes the dose of an existing medication. The current systems are not automated, and there is still room for human error.

In one recent implementation, the Medication Reconciliation document is a plastic, magnetic folder that contains the individual's important health and medication information. The patient can place this on the home kitchen refrigerator, so that emergency medical professionals would have access to the patient's basic medical information in the event of an emergency. The information recorded in this file would include medications taken, allergies, medical conditions, emergency contact information, blood type, and name of physician.

It would also be desirable to have a single unified system that both keeps the patient records for all the participating patients, and provides access to the patient's health records at remote sites over the Internet.

OBJECTS AND SUMMARY OF THE INVENTION

Accordingly, it is an object of this invention to provide a web-based, i.e., network based, medical records storage and retrieval system that operates means of the web browser installed in a computer, and which avoids the drawbacks and deficiencies of the prior art.

It is another object to provide a means of home interaction between the patient and the health care provider(s), allowing the patient to view and edit the patient's medical record and medical history, to view and change appointments, and to review prescription data including dosages and refill information.

It is a further object to provide a system that provides the medical care provider, e.g., physician, nurse, or emergency response team, with a complete record of the patient's prior treatments, surgical procedures, immunizations, allergies, blood type, and other important data in a manner that protects the patient's privacy.

It is a still further object to provide a limited, read-only view of the patient medical record for emergency purposes.

It is a yet further object to provide the system with a firewall that permits the physician to review and edit the physician's records and the patient's record, and permits patient to review and edit his or her own medical record, but not the physician's records or those of other patients.

It is still another object to provide medical records system that is compatible with automated medical records systems of hospitals, clinics, and physician's offices, and can also be employed where the medical provider employs a manual system.

Other objects are to provide the physician with improved patient through-put; to empower patients with the ability to do so to maintain and manage their own records, and to provide their physicians with complete, accurate medical information; to eliminate the patient hazards in emergency visits by enabling emergency room personnel to access vital patient information using normal Internet access; to minimize or eliminate occurrences or redundant, unnecessary laboratory retesting; and to improve availability to all treating physicians and pharmacists to prevent potentially life-threatening prescription interactions.

In accordance with an aspect of this invention, an automated system is provided for maintaining patient medical records for a plurality of participating patients and which are remotely accessible for reading and editing of the respective patient medical records. The medical records are maintained on a central computer server, which permits access and entry of the patient medical information by authorized persons, i.e., via customer identification and password or similar access code. The system employs a wide-area or global computer network (e.g., the Internet) that permits communication between computer devices connected to it, where each such computer is programmed wit a suitable web browser. The browser on the computer provides a capability for automatic input of patient identifying data when a patient inserts a coded access means into the computer device. In one preferred mode of many possible embodiments, the access means can be a miniature CD-ROM that is inserted into a computer, which then accesses the system server via the Internet, and can also identify the client (i.e., patient) and then point to an access portal of the server. The server incorporates a suitably programmed computer and an Internet connection for connecting with the Internet (or other network), a memory for storing said patient medical records, and software providing data modules to each said computer device into which a respective one of the coded access means has been inserted, where the coded access means corresponds to a respective given patient. In such case, that respective computer device displays a patient log-in screen. The log-in screen has entry spaces that permit the patient to enter that patient's password. Once the password is entered, the patient is provided with access to a series of editable patient history screens. The log-in screen also has an "emergency" button that the patient, or more likely, an emergency response team member, can click onto and thereby access a read-only emergency data screen. This screen displays vital items of patient health data for the respective patient that are sufficient to facilitate emergency care for that patient. This would include blood type, name of primary physician, any allergies or special needs, medications prescribed for that patient with dosages, and existence of advance directives, such as a DNR order or an organ donation request. Medical warning notes could include, for example, that a patient has an aneurism on the brain and has a metal clamp on his carotid artery (so that the patient cannot be given an MRI). The software button for accessing the emergency screen does not require entry of the patient's password.

The participating patients whose records are stored on the system are provided with mini-CD ROMs, magnetic cards, smart cards, RFID cards, or other coded access cards, each having a code element that identifies the respective patient, and another code element that causes the computer device automatically to access the server.

Of course, another patient can also log in to his or her own medical records from the first patient's log-in screen. The screen has a patient ID area where second patient can enter his or her own patient ID or identity code, after which the second patient enters his or her respective password to access that patient's own medical history screens.

According to another embodiment of this invention, the system maintains patient medical records for a plurality of participating patients. The records are remotely accessible by patients and by physicians for reading and editing of the respective patient medical records. The system permits entry of patient medical information by authorized persons, e.g., the patient and the physician, over a global computer network (e.g., the Internet). There are at least one patient-accessed computer and at least one physician-accessed computer. These computers are suitably programmed with a web browser. A server includes a suitably programmed computer with means for connecting with the Internet (or other network), sufficient memory for storing the patient medical records, and software providing software modules to each of said computer devices connected to said server over the Internet. This software provides the at least one patient-accessed computer with a set of patient history screens containing a patient medical record of the respective patient. The software also provides to the at least one physician-accessed computer a set of screens containing a physician medical record of the physician's patient. The server also includes a two-way firewall program that allows both the patient and the physician to access the respective patient medical record for reading and editing, but allows only the physician and not the patient to access the physician medical record. This firewall has the feature that the physician can override the firewall, and allow the physician to send test results, images, etc., to the patient, where the patient requests it and the physician approves. In other words, the physician can temporarily "take down" the firewall. This allows the Doctor to send important information to the patient in a convenient form without having to transcribe or copy it. Under the current law and regulations, i.e., HIPPA, the patient's permission would be necessary for the release of this information.

The patient history screens include a medications screen listing each medication prescribed for that patient and a dosage amount entry for each medication. Other patient history screens can include a visits screen listing for each entry thereon a date of a past or scheduled future visit, reason for the visit, identity of the practitioner, and a software button to permit editing of that entry. An allergies screen may have one or more entries, listing for each entry the identity of a particular allergen to which the patient is sensitive, a level of sensitivity of the patient to that allergen, and a software button to permit editing of that entry. A dietary considerations screen can list for each entry thereon specific food related entry for the respective patient. A family history data screen may list the identity of direct family member(s) of the respective patient, and a software button to access a detail screen concerning the medical history of each such direct family member. A prior illnesses screen may list specific illness(es) affecting the respective patient, status of such illness, i.e., whether current, in remission, recent or chronic. An immunizations screen may list the identity of specific immunization (s) and the date of that immunization for the respective patient. A medical diagnosis screen may listing thereon a diagnostic result of examination of the respective patient. In this case, the diagnostic result can include a medical image (e.g., x-ray) incorporated, in digital form, into that entry. An advanced directives screen may indicate data concerning any patient health proxy, a do not resuscitate (DNR) order, or an organ donation order. In this case, the screen would include an area indicating the location where a written copy of such health proxy is filed. These screens may have an edit button that the patient may click on to edit the data, or to review more detail than are present on the main screens.

On the physician's computer, the physician is provided with the physician medical record of the at least one patient. Here, the screen may include a space or spaces for physician entry of notes concerning symptoms, diagnosis, medical procedures performed, and medications prescribed for said patient by the physician. For the physician-access computer, the set of screens may include a diagnosis dialog box, and this may be provided with look-up menus for selecting a diagnosis nomenclature of the patient by key word and for selecting a diagnosis nomenclature by entry of predetermined diagnosis code. A procedure dialog box has look up menus for selecting a medical or surgical procedure nomenclature for the patient by key word and for selecting a procedural nomenclature by entry of predetermined procedure code. The physician's screens may be coupled to the hospital billing computer to facilitate preparation of bills in a form acceptable to health insurance companies.

The above and many other objects, features, and advantages of this invention will become apparent from the ensuing detailed description of a preferred embodiment, which is illustrated in the Accompanying Drawing Figures.

BRIEF DESCRIPTION OF THE DRAWING

FIG. 5 shows a patient account information screen, with a facility to add a member or members.

FIG. 6 shows a patient general information screen.

FIG. 7 shows a patient medical information screen.

FIG. 8 shows a more detailed version of patient general information screen of FIG. 7, including entry editing facilities.

FIG. 9 shows a version of the emergency medical data screen as accessed by the patient.

FIG. 13 shows a patient immunizations information screen with immunization data.

FIG. 14 shows a patient advanced directives screen.

FIG. 15 shows a detail advanced directives screen indicating organ donor data.

FIG. 17 shows a visit information screen for physician access to patient visit information for review and editing.

FIG. 18 shows a screen with payment information and patient health proxy information.

FIG. 19 shows a physician screen for entering notes concerning the patient.

FIG. 20 shows a physician screen with a list for accessing diagnosis nomenclature and standard diagnosis codes.

FIG. 21 shows a dialog box for quick entry of nomenclature and codes in respect to the screen shown in FIG. 20.

FIG. 22 shows a physician screen with a list for accessing procedures, i.e., medical treatments, given to the patient.

FIG. 23 shows an assist dialog box for quick entry of common phrases or codes into the entries of the physician screens of this embodiment.

DETAILED DESCRIPTION OF A PREFERRED EMBODIMENT

Figure 1:
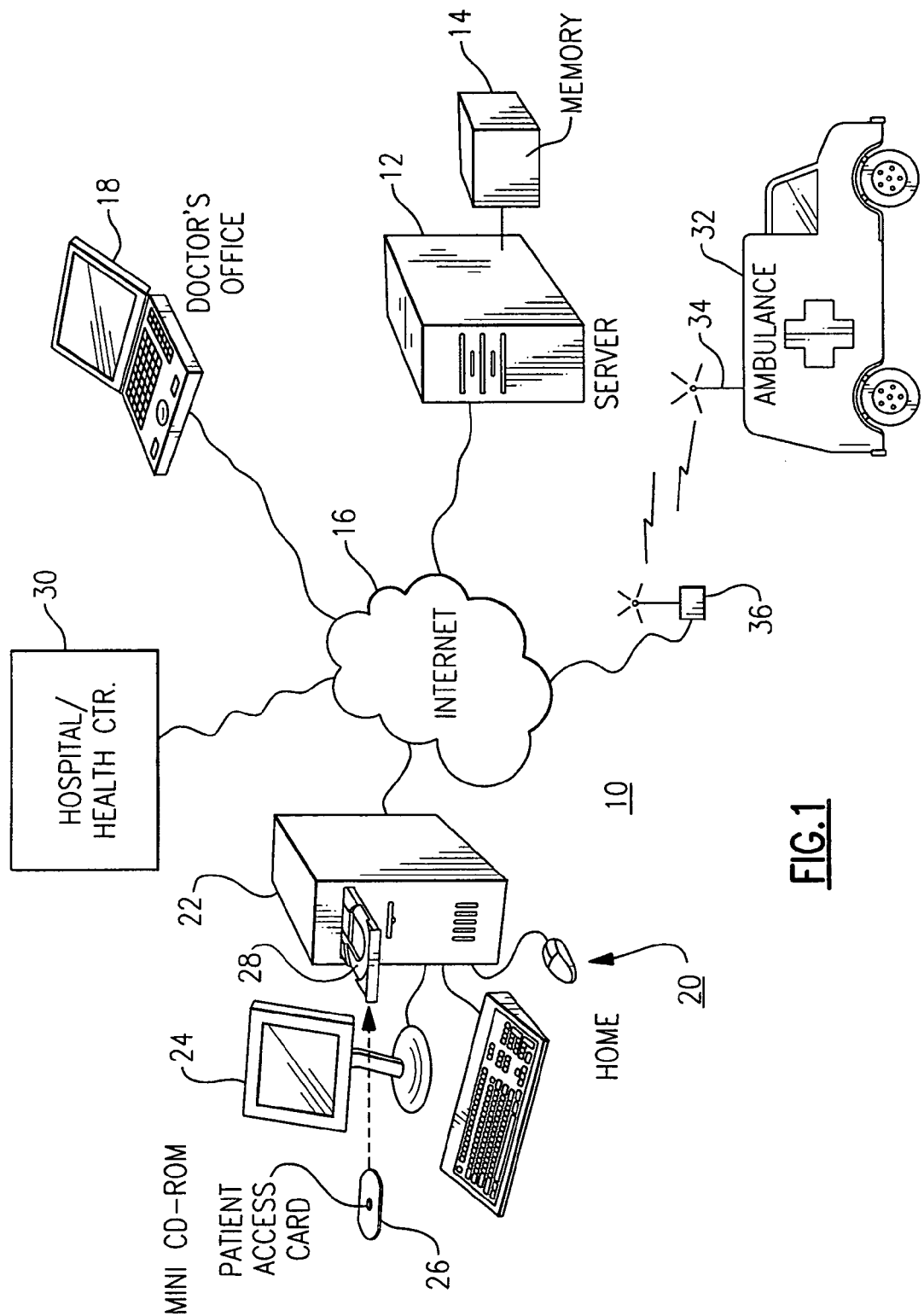
FIG. 1 is a schematic diagram of a medical records and data arrangement according to one preferred embodiment of the present invention.

Now with reference to the Drawing, FIG. 1 shows a basic arrangement of the health care records system 10 according to one embodiment of the invention, which permits the patient access to his or her own medical records and also permits the treating physician(s) to enter health care information about the respective patient, and also to review the patient record. At the heart of the system 10 is a server 12, comprised of a computer with sufficient memory 14 capacity to store the health care data for all participating patients. The server computer 12 has a connection to the Internet 16 in this embodiment, which serves as a global computer network for sharing information with other participating computers on the network. Illustrated here is a computer 18 located at a doctor's office, on which a treating physician can enter data about his or her patient, and on which he or she can review the patient file that is kept on the server 12. The participating patient may access the system 10 by means of a personal computer 20 arrangement, which here has a main computer 22 as well as a monitor 24 on which the various patient screens generated by the system will appear. A patient access card 26, which may be a mini-CD/ROM in this embodiment, can be used by the patient to access the patient's health care files, as described in detail later. The mini-CD/ROM card 26 can be inserted into a CD/ROM drive 28 of the computer unit 22 to access the system, and the card 26 basically contains a code that accesses the server 12 over the Internet 16, and a code that identifies the particular participating patient. A log-in screen appears on the monitor 24 which permits the patient to enter his or her name and a confidential password or PIN so that the patient can access further health care record screens. Of course, the patient can access the system 10 from any computer that has Internet access by inserting the mini CD/ROM card 26 into the CD drive of that computer. As will also be described later in the event that the patient is unable to enter his or her password of PIN, for example, if the patient is injured or unconscious, another person, such as a paramedic or a member of an emergency response team, can insert the patient's card 26 into a computer, and will be able to access an emergency data screen. The latter is a read-only screen, with items of the patient's medical or health care data that would be important in rendering assistance to the patient, such as patient's blood type, known allergies, medications, prior diagnoses and treatments, next of kin, medical warning notes, and existence and location of an advanced directive, such as organ donor data.

In the event that computer Internet access is not available at a hospital emergency room, the fax transmission of the emergency data is possible. The patient's emergency data can be obtained by phoning a 1-800 number printed on the card 26, and the data will be sent immediately by fax. Here, provisions would need to exist to preserve the confidentiality of patient medical information.

It is also envisioned that the patient be able to access the system using a WiFi connected device, or using a cell phone of the type that has Internet access. In either case, the patient can easily access the medical record to enter dosage changes, prescriptions, and treatments right on the cell phone or other device. The patient would be carrying this cell phone or other hand held device in pocket or purse, and it would be available in case of emergency. This feature makes it possible for the physician, health care provider, emergency medical personnel, police or fire department, case worker, or other responder to obtain the patient's medication, allergy, vaccination, and treatment history, name of physician, and other emergency contact data by accessing the server 12 from the patient's hand-held device.

Beyond what is specifically shown in FIG. 1, a number of computer devices located at any of a number of hospitals, clinics, and health care centers would be participating and likewise have Internet access to the system. Here, one typical health care. 30 is shown. An emergency response team may have immediate access via a mobile computer located in the team's ambulance 32 or other emergency vehicle, which may employ a wireless (i.e., radio) device 34 to communicate with another wireless station 36 to access the Internet.

Figure 2:
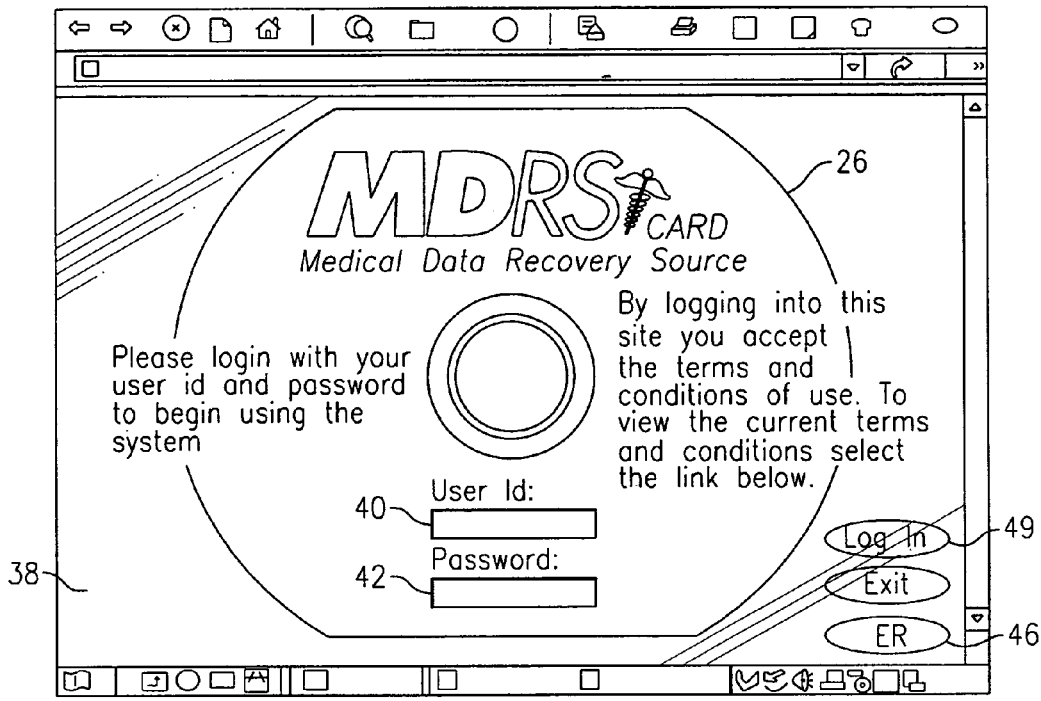
FIG. 2 is a screen view of a patient access screen according to this embodiment.
Figure 3:
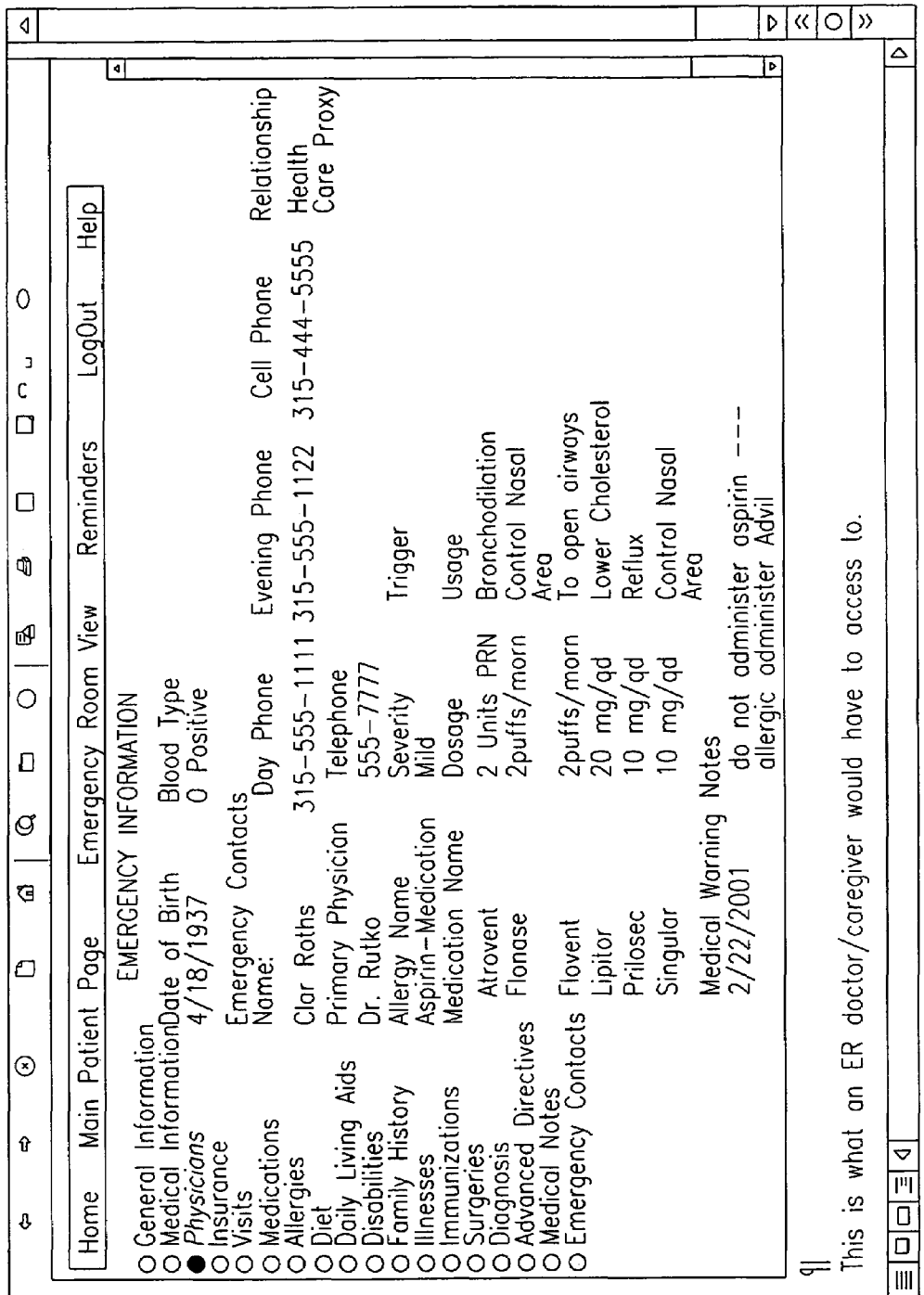
FIG. 3 shows a patient emergency medical data screen, as accessed by emergency services or emergency room personnel.

FIG. 2 shows a log-in screen 38 that appears on the monitor 24 when the card 26 is inserted into the drive 28. In this embodiment, an image of the CD/ROM card 26 appears including a log-in box 40 where the patient may enter his or her patient log-in name or identification as used for logging in, and below that a password box 42, where the patient may enter a password or PIN. In a preferred arrangement, a machine-readable code for the patient's log-in name is carried on the card 26, so that the patient's log-in name automatically appears as a default text in the box 40. This is an important feature for emergency purposes as will be discussed shortly. In addition, it permits other patients to access their own records by entering their own respective log-in names and passwords. When the patient log-in name and password are entered in the respective boxes 40 and 42, then the patient may click on the soft log-in button 44, to go to the patient's medical record screens. An emergency or ER button 46 also is located on the screen 36. Here, when the patient log-in name is entered in box 40, then clicking on the ER button 46 takes the computer to a special emergency medical screen 48 which is illustrated in FIG. 3. In this case, the patient password is not needed. This makes it possible for an emergency response team member, or a family member or neighbor who needs to assist in an emergency, to obtain crucial medical information by simply inserting the card 26 into the computer and then clicking onto the button 46. Emergency medical personnel are trained to look for emergency medical information cards and documents when encountering an unconscious or helpless patient, and would find the card very quickly if the person has it in wallet or purse or in a pocket.

The emergency data screen 48 of FIG. 3 is a read-only screen, which cannot be altered or edited directly, but contains some of the data from the patient's files that is useful, or necessary, for treating the patient in an emergency. In addition to general information such as the patient's name, age, and address, this screen provides the patient's blood type, e.g., "O-positive", the name of the patient's primary physician, immunizations, prescribed medications (including dosages), allergies, and family or other personal contact information. Insurance provider information may also be provided here.

Figure 4:
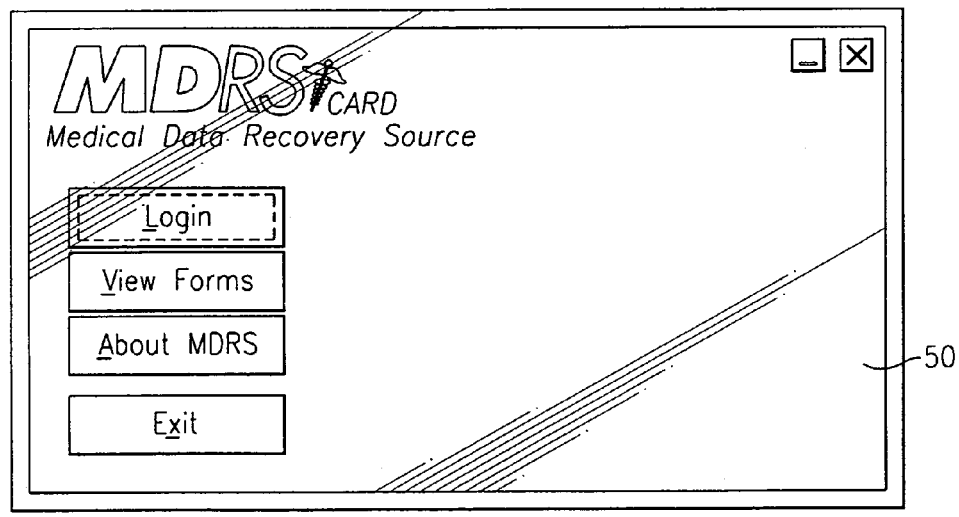
FIG. 4 shows a general access screen that leads to further screens including a log-in screen.

For normal viewing and updating, the patient would typically enter the password into the box 42 and click the button 46. This will bring up the patient's editable health care screens for patient access. Clicking on button 46 brings up an initial screen 50 (FIG. 4) which has buttons for various selections, including logging in, viewing forms, reviewing other information about the system, or exiting and terminating the session. Here, the patient can bring up for viewing and printing out application forms for installing initial information. The forms can be pre-printed to collect initial information. The forms can be completed in pencil or ink and brought to the physician's office for entry, or for entry by a family member if the patient is not comfortable working with the computer. A hold-harmless agreement is viewable here. Software for viewing .pdf files can be installed. An electronic self-help book is also available from this or other screens.

At the end of any editing session, upon logging out, the system returns a confirmatory email message to the patient for each update event showing who performed the update, and when it occurred. All data is entered on the system server 12 and is archived in the memory 14, so an electronic audit trail is preserved of all changes to the patient's medical record. All data are obtained by retrieval from the server 12. A 128-bit encryption system is employed for security of the patient's health care data. The information is immediately available after each update, i.e., in "real time". The system can also allow the member to grant a proxy to a family member, friend, or neighbor, so that the proxy can be in charge of the patient's medical record. In that case, the proxy would have a distinct identity, i.e., a separate password, so that the system is aware of who it is that is updating or accessing the records.

An initial patient account screen 52 is illustrated in FIG. 5. Here the patient's name appears in a box 54 with a down arrow 56. By clicking on the down arrow, a list of other patients, e.g., other family members, may appear. It may be necessary to enter a respective patient password, which can be done on a small pop-up dialog box (not shown), to view a different patient medical records. It is also possible to add a new patient at this screen. By clicking on the GO button next to the patient name box, the patient general information screen 58 (FIG. 6) will appear. Clicking on the new patient button 62 at the bottom of the screen will also bring up a blank version of the general information screen 58 permitting data about a new patient to be entered. Here family members can be added. A basic family membership would cover, e.g., two adults and up to four minors. The forms can be pre-printed so that the new member can fill out the forms and collect information before installing the initial information about the new patient into the system.

The general information screen 58 contains basic general information about the participating patient, such as name, address, phone numbers at home and work, employer name and address and other contact information such as email address. An EDIT button 60 appears on this page, and on subsequent pages as well, which gives the patient a long view of the information from that page and allows the patient to update or change the data for that view. For example, the patient can correct the address or phone number here. A listing of other screens or pages appears at the left of this screen. These entries are in hypertext, and the patient can reach the subsequent screens by clicking on the respective name or title.

A general medical information screen 64 (FIG. 7) gives the patient name, plus other general medical data about the patient, i.e., blood type, weight, height, eye color, language(s) spoken by the patient, and race. Other items could be included here. By clicking on the EDIT button 60, a long view of this screen is achieved, as shown in FIG. 8. The above information, plus additional general medical data, appear here in a form that can be changed or entered by the patient. Here the additional data include information about vision, dentistry, use of prosthetics, tobacco and alcohol use, and other categories of information.

If the Physician's screen is selected, then the emergency data appears as shown in FIG. 9, which corresponds to the emergency screen that was discussed in respect to FIG. 3. This screen lists important medical or health information about the patient, including the items discussed previously such as allergies and medications, which the emergency doctor or health care provider would need access to. In addition, this screen contains health care proxy data, and quite importantly, medical warning notes such a high sensitivity to certain drugs or treatments.

An Insurance Provider screen (not shown) would list the patient's health care coverage, by carrier(s), type—primary or secondary—, plan number, and contact information.

Figure 10:
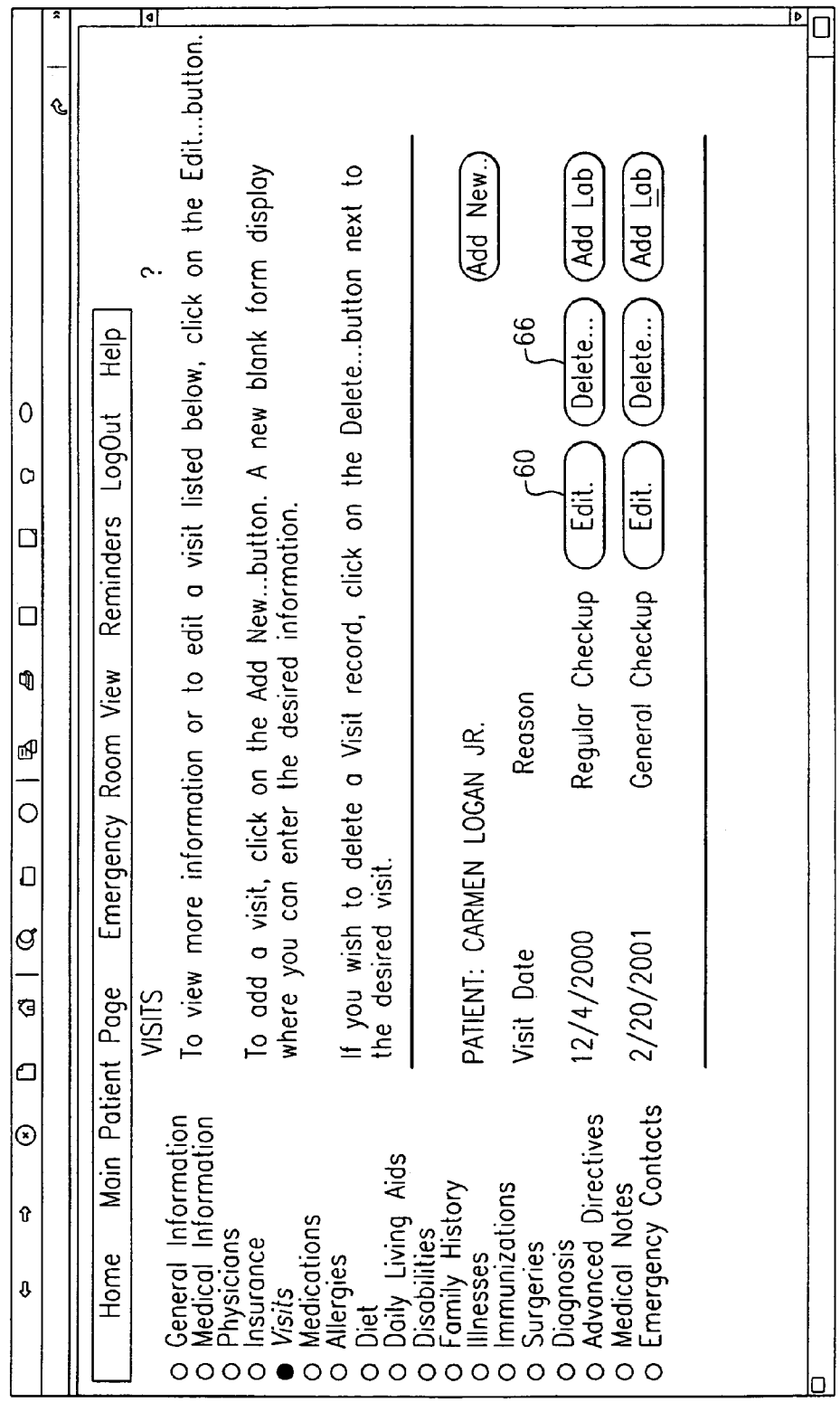
FIG. 10 shows an insurance provider information screen.

A visits screen (FIG. 10) provides information about each visit to the health practitioner, including for each entry the date of the visit, reason for visit (regular checkup, etc.) and an edit button 60 to bring up a detail screen for editing the material about that entry. In this embodiment there is also a delete button 66 for deleting an entire entry from the visits screen.

Figure 11:
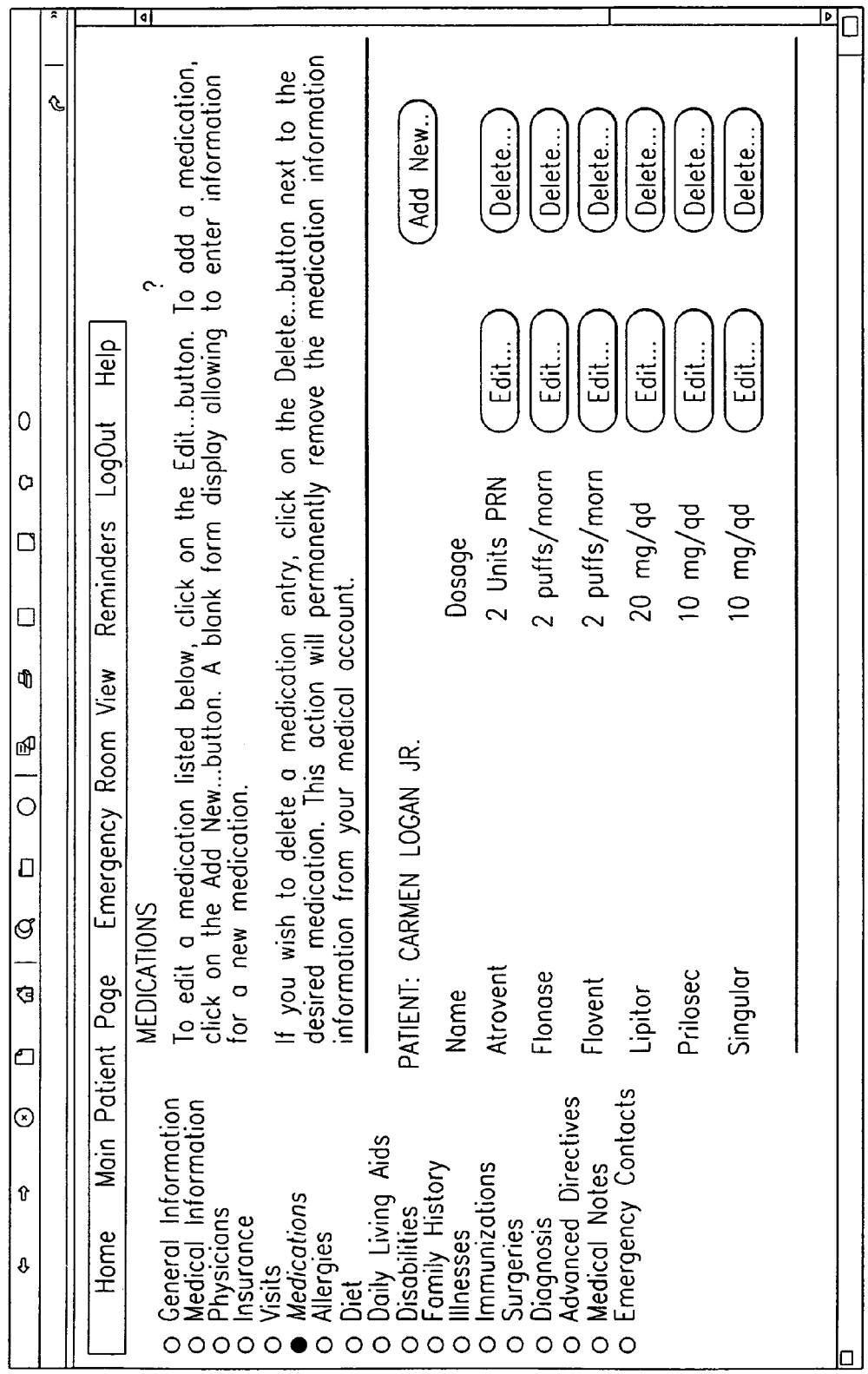
FIG. 11 shows a patient medications information screen with prescription and dosage information.

FIG. 11 shows a medications screen with a number of line entries, each containing the information about a medication that has been prescribed for the patient. In each line there are separate column entries for name of each medication and for the dosage plus the directions on how the medication is to be taken, e.g., milligrams and times per day. Here also, there are soft buttons for editing and for deleting the respective entries. Here there is also a button for adding a new entry, i.e., if an additional medication is prescribed. This screen is important for any physician as it will let him or her know what medications the patient is already exposed to so the physician can avoid giving any contra-indicated medications. Also, the screen serves as a reminder to the patient and to a pharmacist about the drugs and dosages prescribed for the patient.

Figure 12:
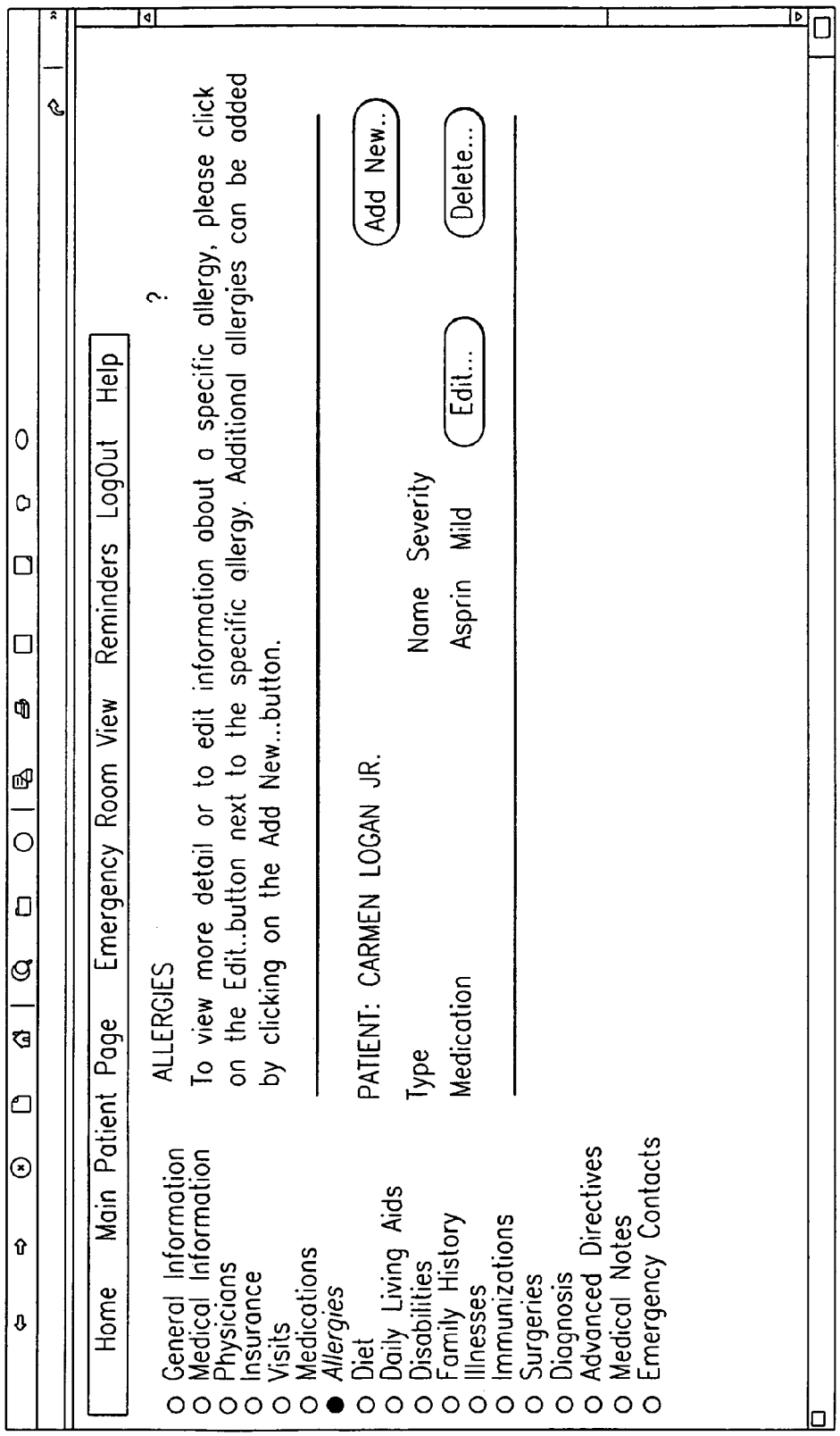
FIG. 12 shows a patient allergies information screen.

An allergies screen is shown in FIG. 12, listing for the patient any known substances for which the patient has any allergic reaction. The severity of the allergy is also given. In this example, the patient listed here is shown to have a mild allergy for Aspirin. Each entry can be edited or deleted, as described before, and an additional allergy can be listed by first clicking on an Add New button.

Similar screens can show, for example, dietary considerations that the patient is supposed to observe, e.g., low carbohydrates, low salt, or high fiber; or may show daily living aids that have been recommended for the patient, such as an air purifier. Any appliance or durable medical equipment to help the patient may be listed here, including mobility equipment or special bathroom equipment.

Disabilities may also be listed on a disabilities screen, e.g., hearing loss, vision problems, or mobility limitations. Multiple disabilities may be displayed, by type and name.

A family history screen, also not shown here, may include entries for the patient's parents, other ancestors, and siblings. This is considered important information, and allows the physician to see previous existing health conditions of family members, and notes of what diseases or problems might have affected them. Here, a long view of each family member can be accessed by clicking on an edit button near the family member's name, and this long view would show the name and relationship of the family member, and which disease had affected him or her.

An illnesses screen, also not shown here, lists recent or chronic illnesses that have affected the participating patient, each line listing the name of illness, type, and status (e.g., current or not) for the particular condition.

An immunizations screen is shown in FIG. 13, listing for the patient each immunization by type, age of patient when inoculated, and date. This lists also multiple inoculation, such as the inoculation for diphtheria, tetanus, and pertussis. By making the physician aware of the status of each immunization, new immunizations or booster shots can be given in timely fashion for the patient, but unnecessary re-immunizations can be avoided.

A surgeries screen (not shown) lists each surgical operation performed or scheduled for the patient, with the date, type and other information germane to that specific surgery. Each medical diagnosis can be shown on a medical diagnosis screen (also not shown here) which may indicate whether each diagnosis is short or long term.

An advanced directives screen is shown in FIG. 14. This screen indicates whether the patient has made any sort of advanced directives which would be carried out in the event accidental death or patient's long term degenerative condition. Where the screen shows that an advanced directive exists, the patient or physician can click on the edit button, which brings up a long view, as shown in FIG. 15. In this example the advanced directives include a DNR or do-no-resuscitate order, and may list organ donations authorized by the patient. This also indicates the location where the patient's written directive is located, e.g. "St. Joseph's Hospital." A health care proxy, i.e., the patient's spouse, son or daughter, can also be listed here so that the person may be contacted if needed to make a critical health care decision for the patient.

Medical warning notes may be listed on a respective individual screen, such as "do not administer aspirin". These data appear on the emergency screen, i.e., FIG. 3, and are important for emergency room personnel.

A Reminders screen can include upcoming medical appointments, e.g., the date and place of the next appointment with a physician, date when medications are to expire, date when a test is to be taken. The information here will automatically generate reminder email messages for the patient about seven days prior to the given appointment or other scheduled event. Email reminder messages are sent some predetermined time before medications expire.

Other screens may be added to these, depending on the patient's medical needs. For example, a screen may be added for dental issues, and screens may be added for vision and optometry, or for physical therapy. The system is intended to be quite flexible, and screens can be added as need be to suit each particular patient.

The system 10 includes a firewall program in the server 12 that recognizes the participating patients and also recognizes the physician or other practitioner, and permits the practitioner to access and edit the physician's office records and the patient records, and also permits the patients to access and edit their own records but not those of the physicians or of other patients. The physician can override this firewall program for a given item of patient data, for example, health testing results. The system requires first that the patient ask the physician for the information, and the physician would enter data in a text box on the screen to confirm that the patient had requested the data. Then the patient temporarily has access to the screen of data or to some portion of the screen.

The patient screens have been described just above, and the following is a description of the various screens that appear on the physician's computer 18 so that he or she can access his or her patients' records and update them, as need be.

Figure 16:
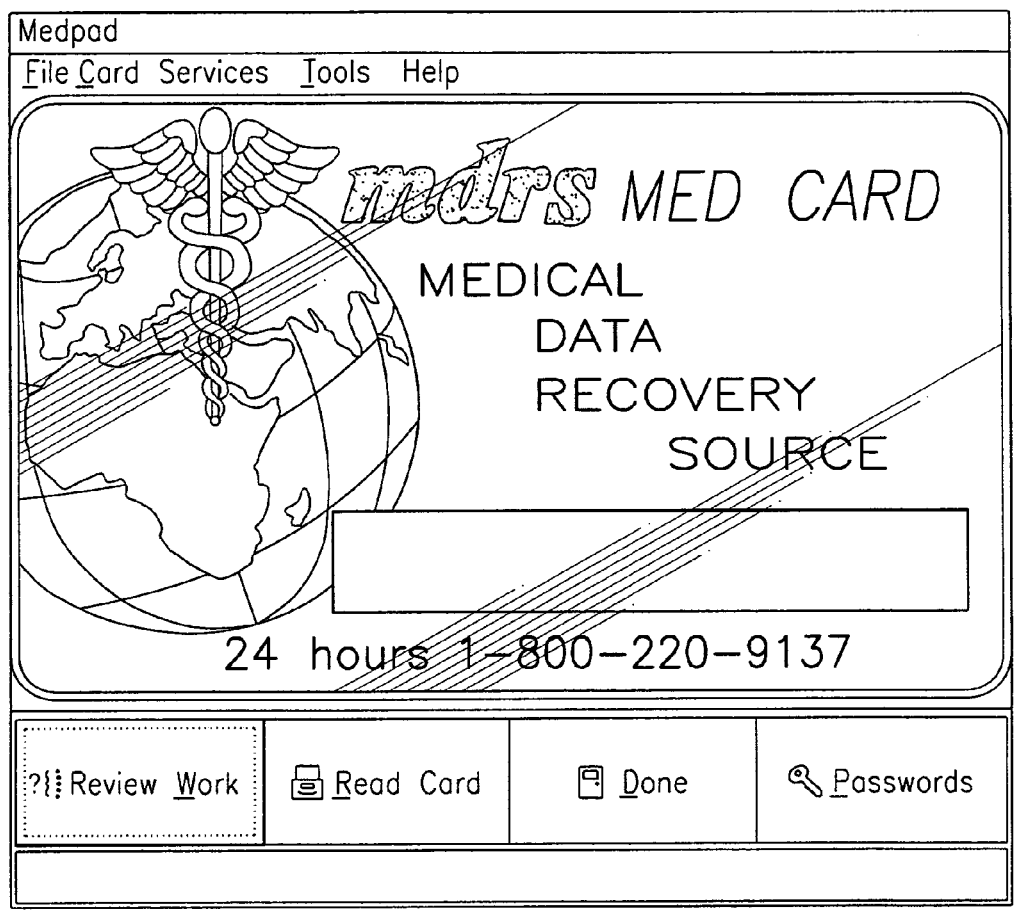
FIG. 16 shows a physician access screen as appears on the medical practitioner's computer.
Figure 17:
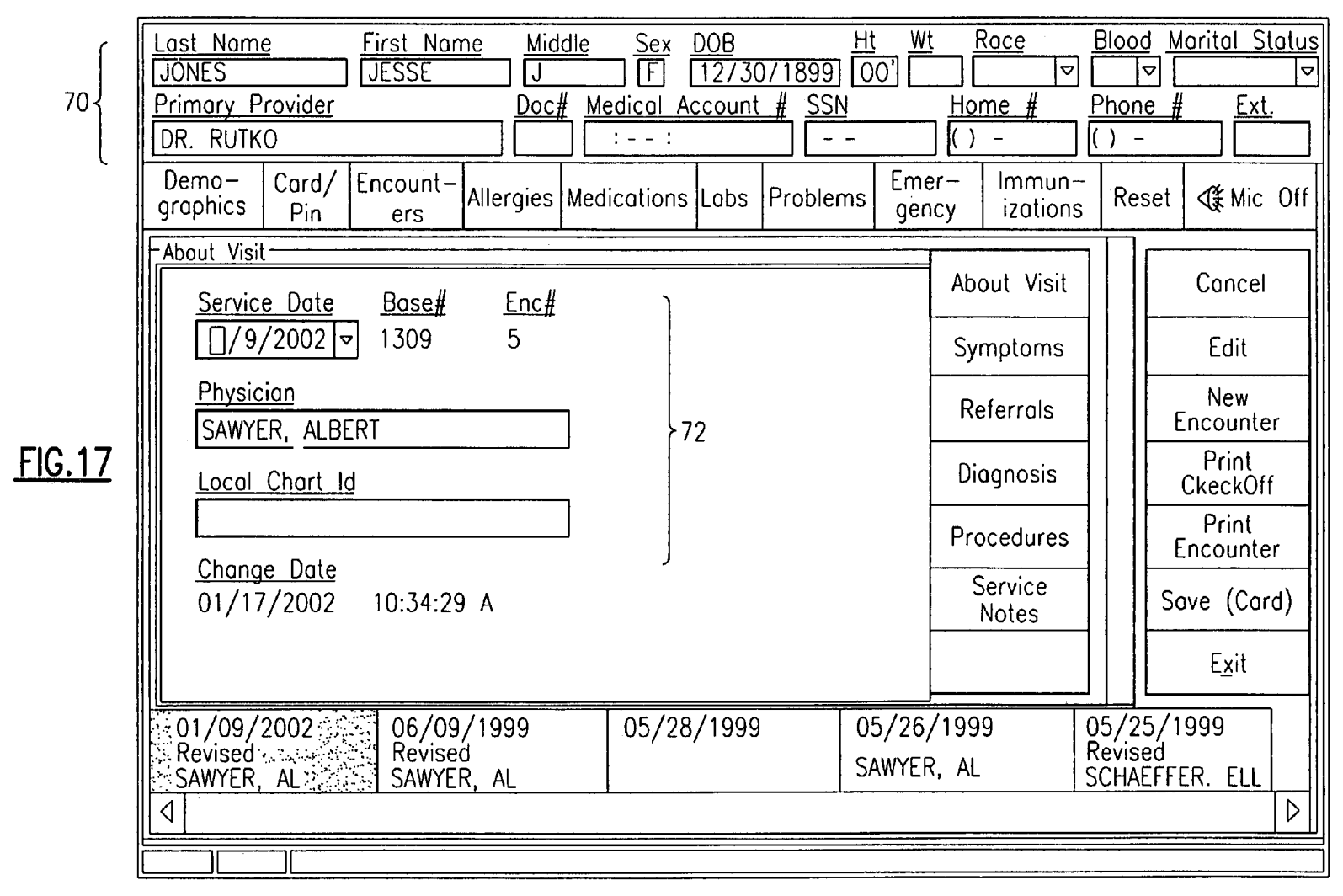

A physician review page, i.e., screen is shown in FIG. 16. This screen provides access to the physician side of the patient records, where the physician can review the patient data but the patient cannot directly view the physician's work. This system runs in a fashion similar to that described above with respect to the patient's CD/ROM access card, but is installed to act based on the physician's personal password. The system may be designed to operate with Smart Card technology, and may be used on a Med Pad computer, i.e., a laptop used without a keyboard, but having a touch screen, or may employ a smart card reader, and may incorporate voice to text technology. In FIG. 16, as single identifier, i.e., a medical health account number, is entered to track a given patient. Each patient is assigned a specific, unique MHAN, which is used throughout the system. This may be the same as the patient's social security account number, but it is preferred to use a different number for reasons of preventing unauthorized access to the customer's credit and banking accounts. This same tracking number may be used for billing purposes as well. The review page may indicate if the patient is still in the physician's office or if he or she has left. Various software buttons are shown on this page that permit selection of various features. By selecting the Review Work button, the system takes the computer 18 to a patient visit page (FIG. 17) for the given patient. This screen can track the last fifteen office visits for that patient. A bank of soft keys are shown here, labeled "About Visit", "Symptoms", "Referrals", "Diagnosis", "Procedures", and "Service Notes." A group of spaces 70 is provided for entries including name of patient, date of birth, height, weight, blood type, and other vital statistics, name of primary care physician, the patient's medical history account number (MHAN), phone numbers, and other identifying data. These entries may be editable by the physician. Below that is a zone 72 for entry of information about the specific medical visit, giving the physician's name, date, and other items concerning the patient visit. This screen may track the last fifteen doctor's office visits of each patient.

Figure 18:
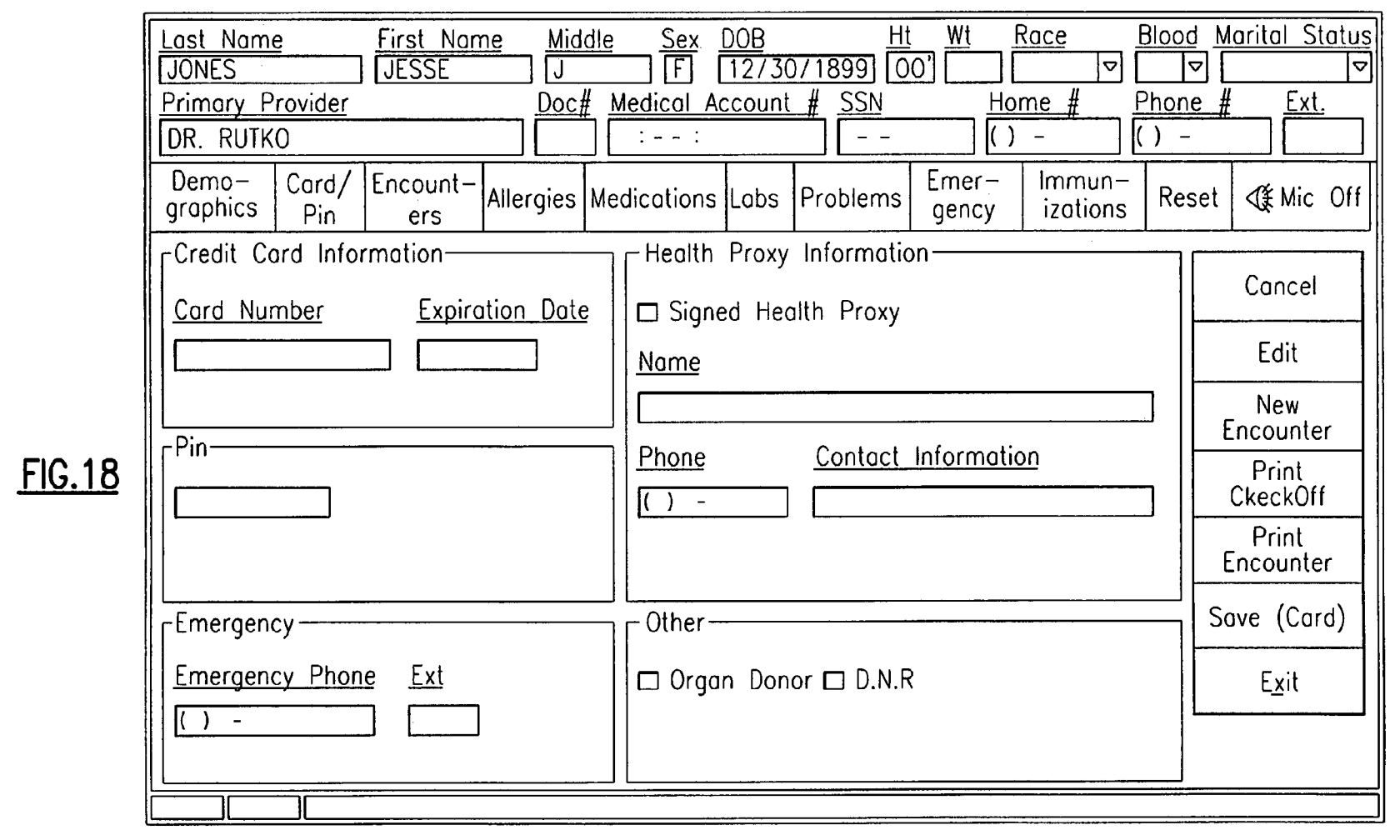

FIG. 18 shows a screen for patient financial data. This view is a Smart Card view for credit card and PIN number entry, where the monies are to be collected by means of a credit card or debit card (such as from a health savings account or HSA). Health proxy information also appears on this screen, including entries for the name and address of the individual named by the patient, and contact information. Other information, such as the existence of organ donor or DNR orders, can appear on this screen. Details about these items will appear on subsequent screens.

Figure 19:
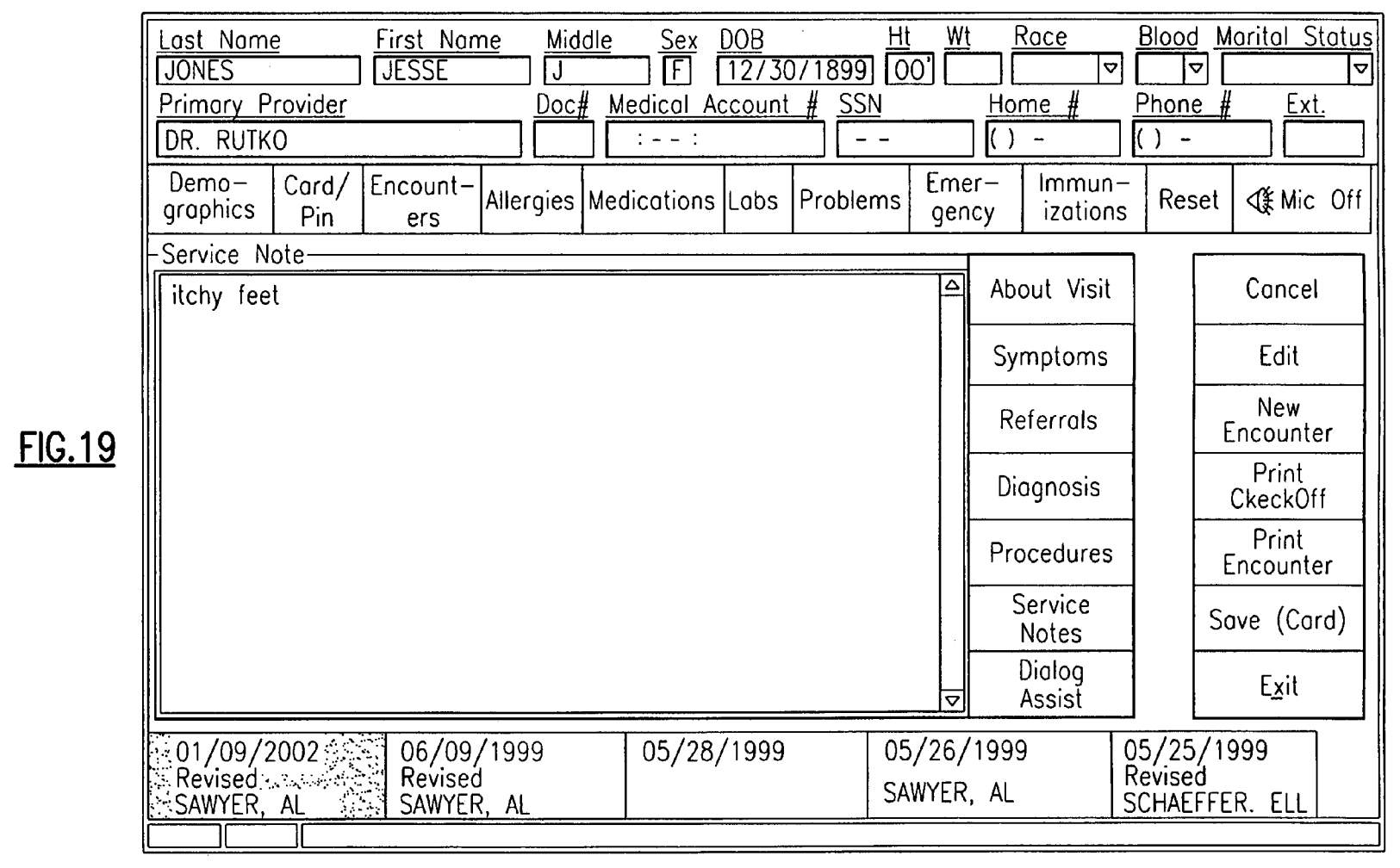

FIG. 19 shows a Service Notes screen, where the physician can enter specific observations made about the patient at the office visit. In this case, the patient had reported "itchy feet" to the doctor. Any of a wide variety of other observations or doctor recommendations can be indicated here. Specific symptoms can be listed on a subsequent Symptoms screen, which may have a similar layout. Another similar screen, not shown here, lists Referrals, i.e., other practitioners recommended to the patient.

Figure 20:
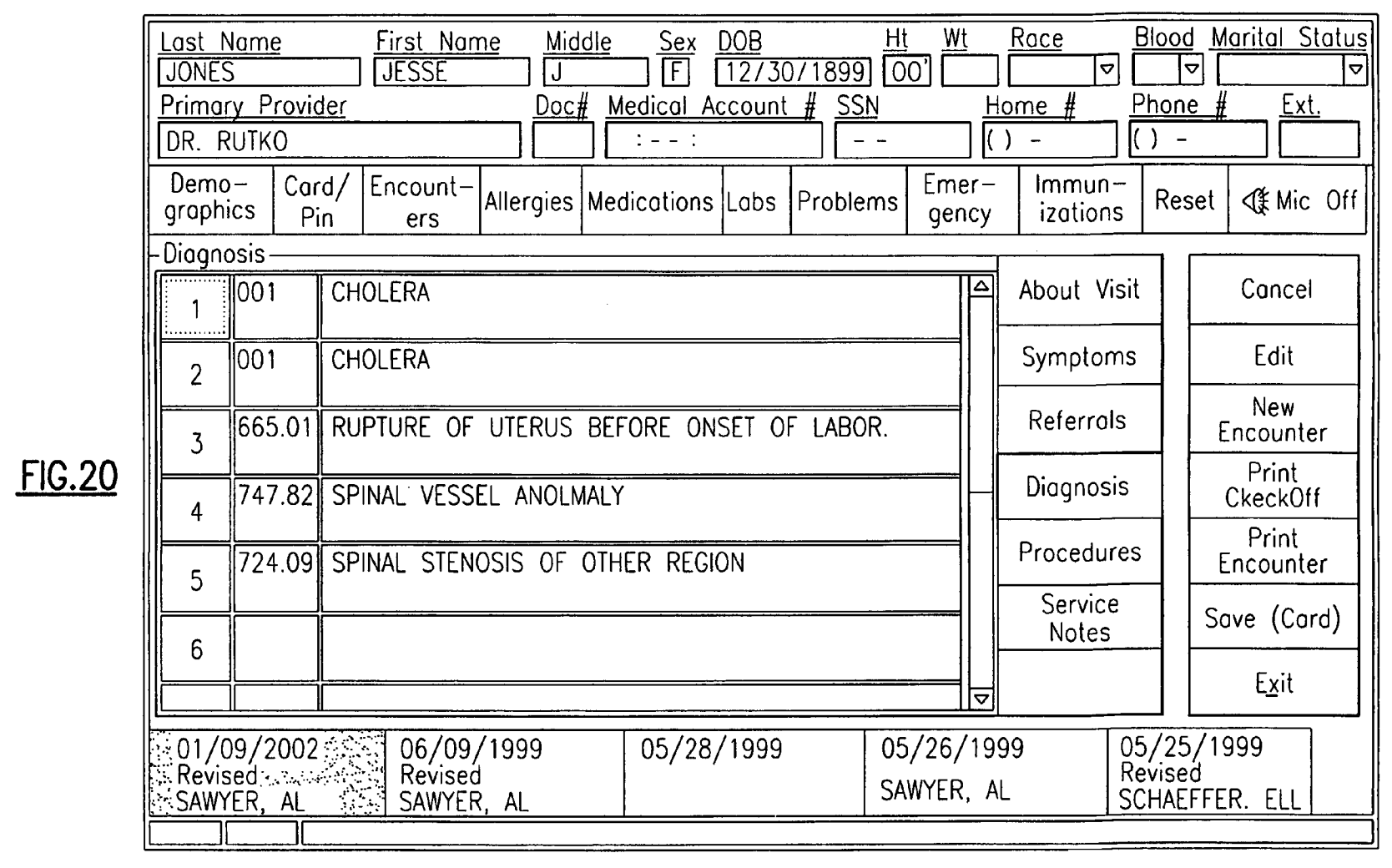
Figures 21, 23:
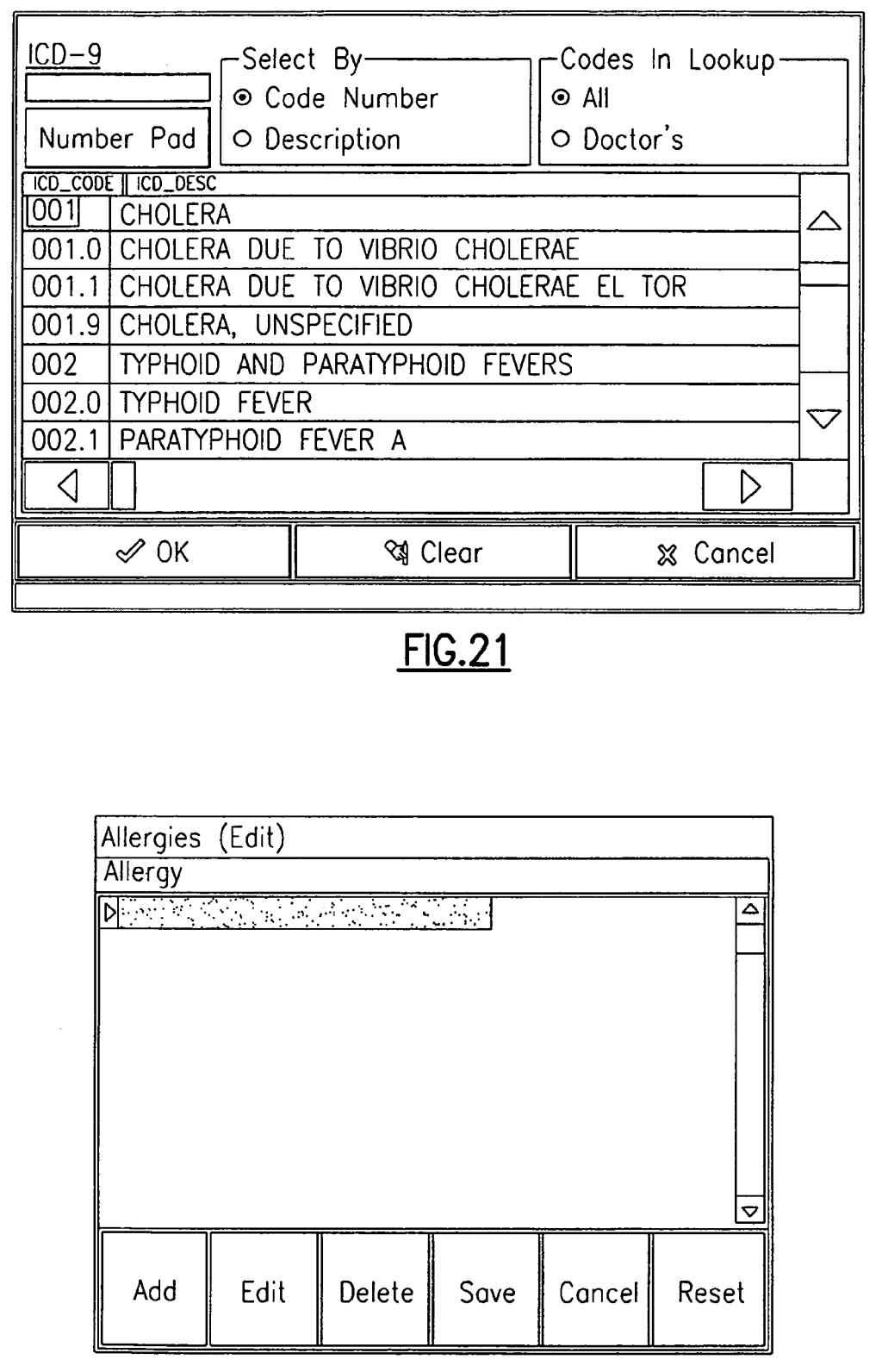

A Diagnosis list screen is shown in FIG. 20. Here the diagnoses made by the physician can be entered in list form. The number of diagnoses can be quite large, as the screen has capability for scrolling beyond those actually displayed. For each diagnosis entry, there is a space for a code (here, ICD-9) and a space for the standard nomenclature for the diagnosed medical problem. A help box for this screen is shown in FIG. 21 to assist the physician in entry of the ICD-9 code and ICD descriptive nomenclature for each diagnosis. The entries can be selected by either code number or description, and a code look-up provision is included. This can be narrowed down to the list of the items that the physician is most likely to encounter. Here, the physician would scroll down to the intended item entry, and he or she could simply click on the item and then click on the "OK" buttons to make the entry in the diagnosis screen.

Figure 22:
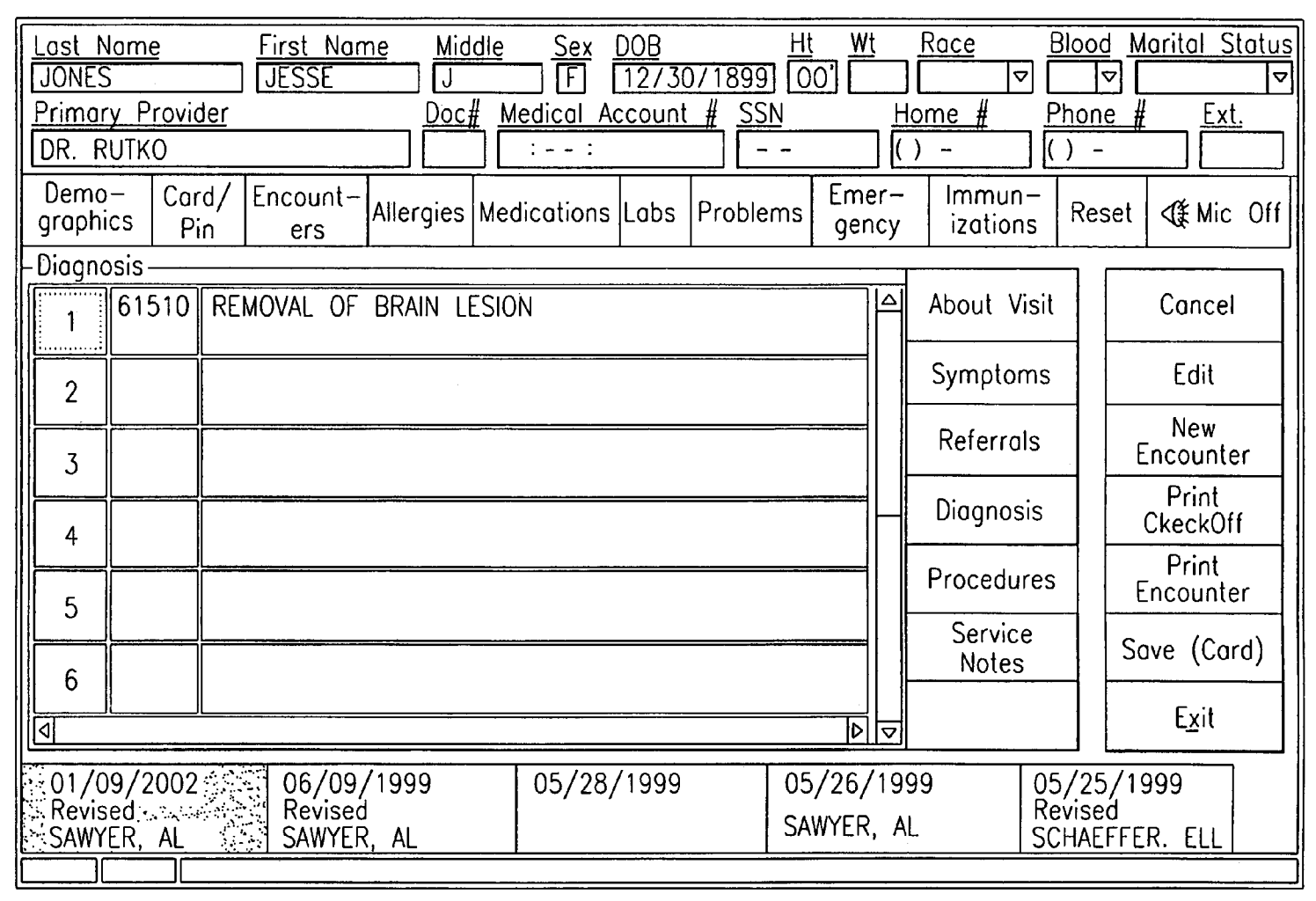

FIG. 22 shows a screen for entering medical or surgical procedures performed in respect to the patient. A procedure may be entered in each space, either by entering a procedural code (CPT-4) or by entering the descriptive nomenclature. Here, a help box similar to that described in respect to FIG. 21 can be employed to assist the physician in entry of the correct procedure data, either by code number or description. This can include a dialog assist box, which can select by common phrases and codes, or by physician notes that the physician may want to use to expedite his or her work.

The lists of allergies for a given patient would be shown on an Allergies screen, which would be similar to those described above, and prescribed medications would appear on a similar Medications screen. To facilitate entry of information, an allergies help box (FIG. 23) has a drop down menu with self-explanatory options for each allergy. The physician then simply clicks on the ADD button to make the new allergy entry. A similar medications help box is used for entry of prescriptions. Here, the entry would list for each medication the date, the name of the medication, strength, quantity, and direction for use. Similar screens may be employed for laboratory work, allergies, problems noted by the physician, and entry of notes for an emergency provider. These include drop down menus, and may be stacked one atop the other for easy viewing.

While not specifically shown here, it is possible to include with the prescription or pharmaceutical information actual images of the doctor's prescriptions, which may be needed by pharmacists. It is also possible to include medical images, i.e., x-rays, sonograms, MRIs, or the like, on the patient's screens or physician's screens, for use in subsequent diagnoses, or to assist in understanding the progress of a disease or of a treatment.

As mentioned before, the firewall protects the physician screens from being accessed or edited except by the physician. The wallet-sized CD-ROM 26, which provides Internet access to the patient's medical records, organ donation information, and other important medical and health information, has multiple levels of protection, so that the patient information will not be accessed without authorization.

On the other hand, the user-friendly technology employed in the system, plus the convenience of the miniature CD/ROM card 26, allow the patient and the authorized physicians to gain access to their medical records on a secure server via the Internet. Specific emergency data can be accessed without the patient's password or PIN. However, all data entered onto the server will be protected through encryption and firewall. The system 10 meets all privacy codes and federal regulations for securing and transporting health care information about private individuals. Because the card 26 that is carried by the patient is used for access and identification, and the health care data are contained on the server at a central location, the medical data are more secure than if they were transferred by hard copy or contained on a computer chip carried on the person of the patient. The information can be presented in a convenient form for the users, e.g., HTML or PDF, or another convenient file format. The system also offers email alert features: The patient can program e-mail reminders to appear for every doctor's appointment, prescription refill or renewal, and other medical incidents that may be important to health care.

The system of this invention may be especially beneficial for at-risk patients, disease management patients, students entering colleges, or persons studying abroad or stationed or traveling abroad. Administrators at HMOs, retirement homes, or universities may distribute the CD/ROM cards to persons enrolled in their programs and facilities.

The system of this invention reverses some of the reasons for poor patient care that have plagued the health care community. By providing each treating physician with current medical history and health care data for the patient, the physician will have knowledge of any prior conditions, any possible allergic reaction or pharmaceutical contraindication. In addition, because records of all prior diagnoses and testing are maintained, the incidence of redundant and unnecessary testing and lab work will be reduced or eliminated. The physician will also see the treatment notes and procedures made by other health care practitioners. The physicians will be freed from much of time demands now made by required documentation, and this will provide more time for spending with the patient. The system also give the patient access to his or her own charts, and allows the patient to check on prescription information, upcoming visits, and other medical data that may affect him or her.

While the invention has been described hereinabove with reference to a preferred embodiment and various alternatives thereto, it should be apparent that the invention is not limited to such embodiment(s). Rather, many variations would be apparent to persons of skill in the art without departing from the scope and spirit of this invention, as defined in the appended Claims.

I claim:

1. A system for maintaining patient medical records for a plurality of participating patients, and in which such records are remotely accessible by participating patients and by physicians for reading and editing of the respective patient medical records, and permitting entry of patient medical information by authorized persons, the system employing a wide area computer network that permits communication between computer devices connected to said network, with the computer devices including at least one patient access computer device and at least one physician access computer device;

each said computer device being suitably programmed with a web browser; and a server including a suitably programmed computer device including means for connecting with said network, a memory for storing said patient medical records, and software providing data modules to each of said computer devices connected to said server over said wide area computer network, and providing to each said patient access computer device for the associated one of said participating patients a set of patient-viewable patient history screens containing a patient medical record of the associated one of said participating patients, and said server also providing to the at least one physician access computer device for each of said participating patients a set of physician-only access screens containing the physician medical record of the associated participating patient, the screens of the set of physician-only access screens being distinct from the screens of the associated set of patient-viewable screens, the physician-only access screens including medical information for said respective patient that is not provided on the patient-viewable screens, each said set being a plurality of screens; and wherein said server also includes a two-way firewall program that allows both the associated participating patient and the physician to access the patient medical record of the associated participating patient for reading and editing, but includes a firewall feature that allows only the physician access computer device and not the associated participating patient access computer device to access the physician-only access screens of the medical record of the associated participating patient; and wherein at least one screen of the physician-only access screens containing the physical medical record of the associated participating patient includes at least one space for physician entry, in said space, of notes concerning symptoms, diagnosis, medical procedures performed, and/or medications prescribed for said associated participating patient by the physician.

2. Medical records system according to claim 1 wherein said patient-viewable screens include a medications screen including each medication prescribed for that patient and a dosage amount entry for each said medication.

3. Medical records system according to claim 1 wherein said patient-viewable screens include a visits screen having one or more entries, and listing for each entry thereon a date of a past or scheduled future visit, reason for said visit, identity of the practitioner, and a software button to permit editing of that entry.

4. Medical records system according to claim 1 wherein said patient-viewable screens include an allergies screen having one or more entries, and listing for each entry thereon an identity of a particular allergen to which the participating patient is sensitive, a level of sensitivity of said patient to that allergen, and a software button to permit editing of that entry.

5. Medical records system according to claim 1 wherein said patient-viewable screens include a dietary considerations screen having one or more entries, and listing for each entry thereon specific food related entry for the participating patient, and a software button to permit editing of that entry.

6. Medical records system according to claim 1 wherein said patient-viewable screens include a family history data screen having one or more entries, and listing for each entry thereon an identity of a direct family member of the participating patient, and a software button to access a detail screen concerning the medical history of such direct family member.

7. Medical records system according to claim 1 wherein said patient-viewable screens include a prior illnesses screen having one or more entries, and listing for each entry thereon identity of a specific illness affecting the participating patient, status of such illness, and a software button to permit editing of that entry.

8. Medical records system according to claim 1 wherein said patient-viewable screens include an immunizations screen having one or more entries, and listing for each entry thereon identity of specific immunization and the date of that immunization for the participating patient, and a software button to permit editing of that entry.

9. Medical records system according to claim 1 wherein said patient-viewable screens include a medical diagnosis screen having one or more entries, and listing for each entry thereon a diagnostic result of examination of the participating patient, and a software button to permit editing of that entry.

10. Medical records system according to claim 9 wherein said diagnostic result includes a medical image in digital form incorporated into the result.

11. Medical records system according to claim 1 wherein said patient-viewable screens include an advanced directives screen having one or more entries, and listing for each entry thereon data concerning a patient health proxy.

12. Medical records system according to claim 11 wherein any entry thereon concerning an advanced order includes an area indicating the location where a written copy of said health proxy is filed.

13. Medical records system according to claim 1 wherein said patient-viewable screens include an advanced directive screen having one or more entries selected from the group consisting of a do not resuscitate order and an organ donation order.

14. Medical records system according to claim 1 wherein said two-way firewall program includes a feature permitting the physician to override the firewall feature and permit the participating patient for a limited time to view limited portions of the physician medical record for said participating patient.

15. Medical records system according to claim 1, wherein the physician-only access screens which include medical information for said respective patient that is not provided on the patient screens include at least one space for posting, within said space, physician entry of notes concerning symptoms, diagnosis, and medical procedures performed, which physician entry of notes do not appear on the patient-viewable screens for the associated participating patient.

16. A system for maintaining patient medical records for a plurality of participating patients, and in which such records are remotely accessible by patients and by physicians for reading and editing of the respective patient medical records of the participating patients, and permitting entry of patient medical information by authorized persons, the system employing a wide area computer network that permits communication between computer devices connected to said network, with the computer devices including at least one patient access computer device and at least one physician-only access computer device; each said computer device being suitably programmed with a web browser; and a server including a suitably programmed computer device including means for connecting with said network, a memory for storing said patient medical records, and software providing data modules to each of said computer devices connected to said server over said wide area computer network, and providing to each said patient access computer device for the associated one of said participating patients a set of patient-viewable patient history screens containing a patient medical record of a respective one of said patients, and said server also providing to the at least one physician-only access computer device for each of said participating patients a set of physician-only access screens containing the physician medical record of the participating patient, the screens of the set of physician-only access screens being distinct from the screens of the associated set of patient-viewable screens, the physician-only access screens including medical information for said respective patient that is not provided on the patient-viewable screens, each said set being a plurality of screens; and wherein said server also includes a two-way firewall program that allows both the respective patient and the physician computer device to access the patient-viewable screens of the medical record of the participating patient for reading and editing, but includes a firewall feature that allows only the physician access computer device and not the patient access computer device to access the physician-only viewable screens of the medical record of said participating patient; and wherein one screen of the set of physician-only access screens containing a physician medical record of the participating patient include at least one space for physician entry, in said space, of notes concerning symptoms, diagnosis, medical procedures performed, and medications prescribed for said participating patient by the physician.

17. Medical records system according to claim 16 wherein said set of physician-only access screens includes a diagnosis dialog box including look up menus for selecting a diagnosis nomenclature of the patient by key word and for selecting a diagnosis nomenclature by entry of diagnosis code.

18. Medical records system according to claim 16 wherein said set of physician-only access screens includes a diagnosis dialog box including look up menus for selecting a procedure nomenclature of the patient by key word and for selecting a procedural nomenclature by entry of procedure code.

19. Medical records system according to claim 16, wherein the notes entered by the physician in said at least one space for physician entry of notes do not appear on the patient-viewable patient history screens of said patient medical record.

* * * * *

UNITED STATES PATENT AND TRADEMARK OFFICE
CERTIFICATE OF CORRECTION

| | | |
|---|---|---|
| PATENT NO. | : 7,640,271 B2 | Page 1 of 1 |
| APPLICATION NO. | : 11/413727 | |
| DATED | : December 29, 2009 | |
| INVENTOR(S) | : Carmen Logan, Jr. | |

It is certified that error appears in the above-identified patent and that said Letters Patent is hereby corrected as shown below:

Col. 4, line 26: "wit" should read --with--.

Signed and Sealed this

Sixteenth Day of March, 2010

David J. Kappos
*Director of the United States Patent and Trademark Office*